United States Patent [19]

Wu et al.

[11] Patent Number: 5,025,004

[45] Date of Patent: Jun. 18, 1991

[54] WATER-DISPERSIBLE POLYMERIC COMPOSITIONS

[75] Inventors: Stephen H. W. Wu, Kingsport; Carol J. Greene, Mt. Carmel; Mahendra K. Sharma, Kingsport, all of Tenn.

[73] Assignee: Eastman Kodak Company, Rochester, N.Y.

[21] Appl. No.: 532,826

[22] Filed: Jun. 4, 1990

Related U.S. Application Data

[62] Division of Ser. No. 205,765, Jun. 13, 1988, Pat. No. 4,960,814.

[51] Int. Cl.$^5$ .............................................. A61K 9/32
[52] U.S. Cl. ..................................... 514/165; 424/59; 424/60; 424/475; 424/477; 424/480; 424/482; 424/490; 524/312; 524/311; 106/170; 106/169; 106/180; 106/194; 106/198; 106/197.2; 427/3; 514/965
[58] Field of Search ............... 424/490, 475, 477, 480, 424/482; 106/170, 169, 180, 194, 198, 197.2; 524/311, 312; 427/3; 514/165, 965

[56] References Cited

U.S. PATENT DOCUMENTS

| | | | |
|---|---|---|---|
| 2,196,768 | 4/1940 | Hiatt | 424/480 |
| 2,718,667 | 9/1955 | Malm et al. | 264/301 |
| 2,776,904 | 1/1957 | Brown | 106/170 |
| 2,881,085 | 4/1959 | Endicott et al. | 424/480 |
| 3,504,082 | 3/1970 | Malm et al. | 424/459 |
| 3,577,514 | 5/1971 | Robinson | 424/468 |
| 3,733,294 | 5/1973 | Keown | 523/310 |
| 4,017,647 | 4/1977 | Ohno et al. | 427/3 |
| 4,177,177 | 12/1979 | Vanderhoff et al. | 106/170 |
| 4,177,255 | 12/1979 | Dannelly | 424/489 |
| 4,330,338 | 5/1982 | Banker | 106/197.2 |
| 4,365,028 | 12/1982 | Leep et al. | 524/364 |
| 4,385,078 | 5/1983 | Onda et al. | 427/3 |
| 4,428,926 | 1/1984 | Keith | 424/473 |
| 4,462,839 | 7/1984 | McGinley et al. | 106/198 |
| 4,518,433 | 5/1985 | McGinley et al. | 106/180 |
| 4,543,370 | 9/1985 | Porter et al. | 523/100 |
| 4,600,645 | 7/1986 | Ghebre-Sellassie et al. | 427/3 |
| 4,647,610 | 3/1987 | Sperry et al. | 524/377 |
| 4,661,162 | 4/1987 | Kurihara et al. | 106/169 |

FOREIGN PATENT DOCUMENTS 2057876 4/1981 United Kingdom.

OTHER PUBLICATIONS

Bulletin 268 of Witco Chemical, Mar. 1978, entitled EMPHOS TM D70-30C.

G. S. Banker and G. E. Peck, "The New, Water-Based Colloidal Dispersions", Pharmaceutical Technology, 5(4), 55-61 (1981).

R. E. Pondell, "From Solvent to Aqueous Coatings," Drug Development and Industrial Pharmacy, 10(2), 191-202 (1984).

M. B. Davis, G. E. Peck and G. S. Banker, "Preparation and Stability of Aqueous-Based Enteric Polymer Dispersions," Drug Development and Industrial Pharmacy, 12(10), 1419-1448 (1986).

F. Gumowski, E. Doelker, and R. Guony, "The Use of a New Redispersible Aqueous Enteric Coating Material," Pharmaceutical Technology, 11(2), 26-32 (1987).

R. K. Chang, C. H. Hsiao, and J. R. Robinson, "A Review of Aqueous Coating Techniques and Preliminary Data on Release from a Theophylline Product," Pharmaceutical Technology, 11(3), 56-68 (1987).

Primary Examiner—Ronald W. Griffin
Attorney, Agent, or Firm—Thomas R. Savitsky; William P. Heath, Jr.

[57] ABSTRACT

Disclosed is a process for preparing polymeric compositions which are suitable for coating medicaments or for use in cosmetic formulations and the novel compositions prepared therefrom. The process makes stable, colloidal, latex-like dispersions of coating polymers which can be readily dried to form polymeric powder materials. The process makes use of a novel combination of a water-in-oil emulsifier and an oil-in-water emulsifier.

45 Claims, No Drawings

WATER-DISPERSIBLE POLYMERIC COMPOSITIONS

This is a divisional of copending application Ser. No. 07/205,765 filed on June 13, 1988, now U.S. Pat. No. 4,960,814.

BACKGROUND OF THE INVENTION

The need and the value of aqueous film-coatings for dosage forms are well documented. Typical examples of publications in this are listed as follows: G. S. Banker and G. E. Peck, "The New, Water-Based Colloidal Dispersions," Pharmaceutical Technology, 5(4), 55–61 (1981); R. E. Pondell, "From Solvent to Aqueous Coatings," Drug Development and Industrial Pharmacy, 10(2), 191–202 (1984); M. B. Davis, G. E. Peck, and G. S. Banker, "Preparation and Stability of Aqueous-Based Enteric Polymer Dispersions," Drug Development and Industrial Pharmacy, 12(10), 1419–1448 (1986); F. Gumowski, E. Doelker, and R. Gurny, "The Use of a New Redispersible Aqueous Enteric Coating Material," 11(2), 26–32 (1987); and R. K. Chang, C. H. Hsiao, and J. R. Robinson, "A Review of Aqueous Coating Techniques and Preliminary Data on Release from a Theophylline Product," 11(3), 56–68 (1987).

In brief, the major reasons for the current high level of interest in aqueous film-coating systems to replace the traditional solventborne coating systems are the demand of environmental protection, increasing cost of the coating solvents, and the availability of several new products for waterborne pharmaceutical coating applications.

The common methods of eliminating or minimizing organic solvents in a coating process for preparing pharmaceutical dosage forms include the following:

1. The coating system employs a solution of coating polymer in a mixed organic and aqueous solvent system such as hydroxypropyl methylcellulose (HPMC) in ethanol/water. This method only partially eliminates the need for organic solvents.

2. The coating system employs an aqueous solution of water-soluble film-forming polymer. This method is limited to water-soluble polymers such as methylcellulose (MC), hydroxypropyl cellulose (HPC), and HPMC. Another limitation is the need of removing a large amount of water during drying and coating processes.

3. The coating system employs an aqueous solution of alkali salt of an enteric polymer such as sodium or ammonium salt of hydroxypropyl methylcellulose phthalate (HPMCP), polyvinylacetate phthalate (PVAP), or cellulose acetate phthalate (CAP).

U.S. Pat. No. 4,017,647 teaches a method for providing enteric coatings on solid pharmaceutical dosage forms in which enteric coatings are provided on solid dosage forms by coating the dosage forms with an aqueous solution of a polymeric substance having carboxy groups in a water-soluble salt form and bringing thus coated dosage forms into contact with an inorganic acid to convert the polymeric substance into the acid form which is insoluble in water.

U.K. Patent Application GB No. 2,057,876 teaches a method of preparing coated medicament-containing cores of a solid unit dosage form with an enteric coating. The coating was applied (e.g., in a coating pan) onto the medicament cores from an aqueous solution of a water soluble salt of a cellulose partial ester of a dicarboxylic acid, the aqueous solution being free from organic solvent, until an enteric coating around each medicament core has been built up. The salt may be a sodium or ammonium salt of HPMCP or CAP.

4. The coating system employs a true latex of film-forming polymer which is prepared by polymerizing selected monomers from a wide variety of essentially water-insoluble vinyl, acrylic, and diene monomers by an emulsion polymerization process. The polymerization process consists of (1) admixing monomers, initiator, surfactant and/or emulsion stabilizer in water, (2) emulsifying the mixture to form an oil-in-water emulsion with monomers in the internal phase, (3) removing air and oxygen from the emulsion, and (4) inducing polymerization to produce a latex dispersion. The coating system employing a true latex is limited to synthetic polymers with water-emulsifiable monomers and purity of the polymer latices in which the residual monomers or other potentially toxic chemicals used in the polymerization process are usually very difficult to remove.

5. The coating system employs the pseudolatex of a water-insoluble film-forming polymer. Pseudolatex is an aqueous colloidal dispersion of polymer which is, for practicle purposes, indistinguishable from a true latex. However, it is prepared by employing a mechanical method of converting a pre-existing water-insoluble polymer into an aqueous colloidal dispersion.

U.S. Pat. No. 4,177,177 teaches a polymer emulsification process comprising intimately dispersing a liquified water insoluble polymer phase at a certain viscosity in an aqueous liquid medium phase (at a certain ratio, and temperature) containing at least one nonionic, anionic or cationic oil-in-water emulsifying agent at a certain concentration, in the presence of an emulsion stabilizer at a certain concentration selected from the group consisting of those hydrocarbons and hydrocarbyl alcohols, ethers, alcohol esters, amines, halides and carboxylic acid esters which are inert, nonvolatile, water insoluble, liquid and contain a terminal aliphatic hydrocarbyl group of at least about 8 carbon atoms, and mixtures thereof, and subjecting the resulting crude emulsion to the action of comminuting forces sufficient to enable the production of an aqueous emulsion containing polymer particles averaging less than 0.5 micron in size. This patent teaches that the disclosed polymer emulsification process is carried out at a temperature of about 40° to 90° C.

U.S. Pat. No. 4,330,338 teaches a coating composition for pharmaceutical dosages. The dosages use a set of FDA-approved polymers with a long history of pharmaceutical and food use. Pseudolatices containing such polymers are used to produce soluble, enteric, or sustained release coatings when the formulations are applied to dosage forms. Various other ingredients besides the polymers are taught to be required in the coating composition. This patent does not teach any art relating to render pseudolatex dispersions to water redispersible solid products.

U.S. Pat. No. 4,462,839 teaches a process for making a polymeric powder which is readily dispersible in water to provide a composition useful for forming an enteric coating on pharmaceutical dosage forms, comprising providing a freshly prepared spherical water-insoluble enteric polymer particles, adding to said dispersion a phosphate salt in an amount sufficient to minimize coalescence of particles during spray drying. Another U.S. Pat. No. 4,518,433 issued to McGinley et al., teaches a similar process except adding acetylated monoglyceride to the dispersion before spray drying to produce the water-redispersible powder.

SUMMARY OF THE INVENTION

The present invention relates to processes which form pseudolatices. More specifically, the present invention is directed to a process for preparing novel, solid, powdered, polymeric compositions which are suitable for coating medicaments. The process of the present invention is also capable of producing an intermediate, aqueous, polymeric, colloidal dispersion which is suitable for use in cosmetic formulations. The aqueous polymeric dispersion is a stable, colloidal, latex-like dispersion of coating polymer(s) which can be readily dried (e.g., spray-dried or freeze-dried) to form the solid, polymeric, powder materials without the need of introducing additional additives to the dispersions as described in the prior art. The present invention is also directed to powdered, polymeric compositions produced by the process of the invention. The dried, powdered, polymeric materials are readily dispersible in water with mild agitation to form a stable dispersion useful for formulating a coating composition for film-coating of medicaments to form solid dosage forms. Accordingly, the present invention is also directed to such solid dosage forms and process for preparation thereof. In addition, the present invention is directed to a method for treating animals in need of treatment comprising administering such solid dosage forms to said animals. As used herein the term "animals" refers to any animal in which it is desired to administer a solid dosage form, including humans.

DETAILED DESCRIPTION OF THE INVENTION

The process of the present invention makes use of a particular combination of emulsifiers. Depending upon at what point an oil-in-water emulsifier is added, the invention can be viewed as two separate processes. Accordingly, the present invention is directed to a process comprising:
(I) Contacting
  (A) an organic solvent system comprising:
    (a) at least one water insoluble polymer, and
    (b) at least one low molecular weight, more volatile than water, and substantially water-immiscible organic solvent,
  with
  (B) a combination of surfactants comprising:
    (i) at least one oil-in-water emulsifier which is polymeric, water soluble or water dispersible, and nonionic, and
    (ii) at least one water-in-oil emulsifier which is water insoluble, anonic or amphoteric, more hydrophobic than said oil-in-water emulsifier, substantially dispersible in said organic solvent system, and compatible with said oil-in-water emulsifier, to result in an organic phase, followed by the optional step of:
(II) emulsifying said organic phase by adding sufficient water to said organic phase while subjecting the resulting mixture to comminuting force to form a water-in-polymer solution emulsion; and adding to said water-in-polymer solution emulsion an additional amount of water effective to result in a phase inversion to form a polymer solution-in-water emulsion, followed by the optional step of:
(III) passing the polymer solution-in-water emulsion through a particle size reduction means such that the water insoluble polymer is in the form of droplets having an average size in the range of about 0.1 to 0.8 μm, preferably about 0.1 to 0.5 μm, followed by the optional step of:
(IV) removing the organic solvent from the polymer solution-in-water emulsion to form an aqueous colloidal dispersion of polymer, and followed by the optional step of:
(V) drying the aqueous colloidal dispersion of polymer to form a water-dispersible powder, wherein, Component (A) comprises about 5 to about 35 weight % of Component (A)(a) and about 95 to about 65 weight % of Component (A)(b), based on the total weight of (A)(a) plus (A)(b); and Component (B)(i) is present in an amount of about 0.5% to about 70% of the weight of Component (A)(a), and Component (B)(ii) is present in an amount of about 1% to about 65% of the weight of Component (A)(a).

In addition, the present invention can be viewed as a process comprising:
(I) Contacting
  (A) an organic solvent system comprising:
    (a) at least one water insoluble polymer, and
    (b) at least one low molecular weight, more volatile than water, and substantially water-immiscible organic solvent,
  with
  (B) at least one water-in-oil emulsifier which is water insoluble, anionic or amphoteric, and substantially dispersible in said organic solvent system, to result in an organic phase, and
(II) emulsifying said organic phase by adding sufficient water to said organic phase while subjecting the resulting mixture to a comminuting force to form a water-in-polymer solution emulsion; and adding to said water-in-polymer solution emulsion an additional amount of water effective to result in a phase conversion to form a polymer solution-in-water emulsion,
wherein,
said water contains at least one oil-in-water emulsifier which is polymeric, water soluble or water dispersible, nonionic, less hydrophobic than said water-in-oil emulsifier, and compatible with said water-in-oil emulsifer, followed by the optional step of:
(III) passing the polymer solution-in-water emulsion through a particle size reduction means such that the water insoluble polymer is in the form of droplets having an average size in the range of about 0.1 to 0.8 μm, preferably about 0.1 to 0.5 μm, followed by the optional step of:
(IV) removing the organic solvent from the polymer solution-in-water emulsion to form an aqueous colloidal dispersion of polymer, and followed by the optional step of:
(V) drying the aqueous colloidal dispersion of polymer to form a water-dispersible powder, wherein, Component (A) comprises about 5 to about 35 weight % of Component (A)(a) and about 95 to about 65 weight % of Component (A)(b), based on the total weight of (A)(a) plus (A)(b); and said oil-in-water emulsifier is present in an amount of about 0.5% to about 70% of the weight of Component (A)(a), and said water-in-oil emulsifier is present in an amount of about 1% to about 65% of the weight of Component (A)(a).

In the first process described above it is preferred that Component (A) comprises about 10 to about 30 weight % of Component (A)(a) and about 90 to about 70 weight % of Component (A)(b), based on the total weight of (A)(a) plus (A)(b); and Component (B)(i) is present in an amount of about 10% to about 50% of the weight of Component (A)(a), and Component (B)(ii) is present in an amount of about 2% to about 40% of the weight of Component (A)(a).

In the second process described above it is preferred that Component (A) comprises about 10 to about 30 weight % of Component (A)(a) and about 90 to about 70 weight % of Component (A)(b), based on the total weight of (A)(a) plus (A)(b); and said oil-in-water emulsifier is present in an amount of about 10% to about 50% of the weight of Component (A)(a), and said water-in-oil emulsifier is present in an amount of about 2% to about 40% of the weight of Component (A)(a).

In some situations it may not be necessary to perform Step III in order to achieve the desired size powder particles after Step V.

In either of the processes described above, in Step II the preferred sufficient amount of water is at least about 45%, and a more preferred sufficient amount of water is about 45% to above 55%, based on the total weight of the polymer solution-in-water emulsion.

Many water immiscible solvent systems are suitable for use in preparing polymer solutions as described above. Preferably, the solvents or solvent systems are more volatile relative to water in order to be removed rather easily from the polymer solution-in-water emulsion, and to leave minimal residue in the latex-like, colloidal polymer dispersion, or alternatively, have permissible residue limits for use in foodstuffs. Typical solvents include chlorinated solvents such as ethylene dichloride, tetrachloroethylene, chloroform, methylene chloride and similar solvents; aliphatic, alicyclic or aromatic hydrocarbons having 5 to 10 carbon atoms; esters such as ethyl acetate; higher alcohols such as alcohols containing 4 to 10 carbon atoms; ethers such as methyl ether and ethyl ether; and combinations thereof; or combinations of such solvents with polar water miscible solvents such as acetone or lower alcohols in ratios which produce an overall mixed solvent which is substantially water immiscible. For instance, isopropanol and ethyl acetate, methylene chloride, ethylene dichloride or chloroform constitute an excellent solvent system for cellulose acetate phthalate. Numerous other substantially water immiscible solvent systems for dissolving coating polymers by various combinations of volatile solvents will be apparent to those skilled in the art. A preferred weight ratio of water immiscible solvent:water miscible solvent is about 2-4:1; more preferred is about 3:1.

Generally, polymers useful in this invention are water insoluble polymers which are soluble in the said solvents or solvent systems at the temperature of the emulsion process (i.e., below the boiling point of water) and inert to the other nonpolymer substances employed in the process. A typical temperature range of the emulsion process of the invention (i.e., Steps I and II above) is about 25° to about 38° C., preferred is about 30° to about 35° C. The temperature range for the other steps of the present invention (i.e., Steps III, IV and V) is not particularly critical and will be apparent to a skilled artisan depending upon the particular equipment employed and other process conditions. A suitable temperature for Steps III, IV, and V is about the same as for Steps I and II.

Typical water insoluble polymers for use in the present invention include:

1. pH-dependent acidic enteric cellulosic polymers: cellulose acetate phthalate (CAP), cellulose acetate trimellitate (CAT), cellulose acetate succinate (CAS), cellulose acetate propionate phthalate (CAPP), and hydroxypropyl methyl cellulose phthalate (HPMCP).

2. Neutral cellulose esters: cellulose acetate (CA), cellulose acetate butyrate (CAB), cellulose acetate propionate (CAP), and ethyl cellulose (EC).

3. pH-dependent basic cellulosic polymers: cellulose derivatives containing functional groups such as cellulose propionate morpholinobutyrate (CPMB), cellulose acetate diethylaminohydroxypropyl ether. Aminocellulose derivatives such as diethylaminomethyl cellulose, 1-piperidyl-ethyl-hydroxyethylcellulose, and benzylamino-ethylhydroxyethylcellulose. Amino acid esters of cellulose or cellulose derivatives such as cellulose acetate diethylaminoacetate.

4. pH-dependent basic polyvinylpyridine and polystyrene derivatives: poly(2-vinylpyridine), poly(4-vinylpyridine), poly(2-vinyl-5-ethylpyridine), and copolymers of these vinyl monomers or blends of these polymers with each other; copolymers of said vinyl monomers with other vinyl compounds such as esters of acrylic and methacrylic acids, acrylonitrile and styrene monomers, particularly, copoly(2-vinylpyridine/styrene) and copoly(2-methyl-5-vinylpyridine/styrene); copolymers containing imidazoline modified styrene such as imidazoline modified copoly(styrene-acrylonitrile), and polystyrenes modified with basic functional groups such as dimethylaminoethyl groups.

5. Maleic anhydride copolymers: poly(methyl vinyl ether/maleic anhydride), ethylene maleic anhydride, styrene maleic anhydride, and various straight chain and branched $C_1$–$C_6$ alkyl esters of maleic anhydride copolymers.

6. Acrylic/acrylate copolymers and acrylic esters: ethylacrylate/methyl methacrylate copolymers of various monomers ratios (commercially available as Eudragit E-30D and Eudragit L-30D).

7. Other polymers may include biodegradable polymers such as copolymers of lactic and glycolic acids and polypeptides and other polymers such as polyesters, e.g., poly(ethylene terephthalate) which meet the above-defined definition for the water insoluble polymers.

It is contemplated that any mixture or combination of water insoluble polymers can be used in the present invention.

All of the above-described polymers useful in the present invention are known in the art and can be made by known techniques and/or are commercially available.

It is important to include at least an anionic, or amphoteric, water-in-oil (W/O) emulsifying agent as described in Step I in the polymer solution phase (organic phase). The W/O emulsifier must be compatible with the O/W emulsifier. The term "compatible" as used in this context means that the two types of emulsifiers are capable of forming a packed or condensed film at an oil-water interface. The W/O emulsifier preferably has a hydrophobic lipophobic balance (HLB) value of between 1 and 8. The amount of the W/O emulsifier is about 1% to about 65% of the polymer weight, preferably about 2% to about 40% of the polymer weight. Preferred W/O emulsifiers are food grade W/O emulsifiers. Typical food grade, anionic W/O emulsifiers useful for such purpose include phosphated mono- and di-glycerides, citric acid esters of monoglycerides, sulfonated esters and alpha-tocopherol hemisuccinate. Typical food grade, amphoteric, phospholipid emulsifiers useful for such purpose include soy phosphatides, phospholipids, lysophospholipids. Examples are monoacyl or diacyl phosphatidylcholine, phosphatidic acid, phosphatidylserine, phosphatidyl ethanolamine, mono- or distearyl phosphatidylcholine, dipamitoyl phosphatidic acid, and the like. The most preferred are Emphos D70-30C (available from Witco Company) and lecithin.

Emphos D70-30C contains a mixture of about 20 weight % triglycerides along with mono- and di-phosphated esters, as well as saturated (about 14 mole % alkyl chains) and unsaturated (about 53 mole % mono-unsaturated and about 33 mole % conjugated unsaturated) with average chain length of 18 carbons.

It is also important to include at least one nonionic, preferably polymeric in nature, oil-in-water (O/W) emulsifying agent either in the organic phase or in the aqueous phase. By the term "polymeric in nature" is meant that the molecular weight is greater than 1,000. The O/W emulsifying agents useful in this invention generally have a hydrophobic lipophobic balance (HLB) value of about 10 or above. The amount of the O/W emulsifying agent is about 0.5% to about 70% of polymer weight, preferably about 10% to about 50% of polymer weight. Typical examples are poloxamers, polyoxyethylene condensation products such as Spans, Tweens and Tergitols, polyoxyethylene sorbitan monolaurate, polyoxyethylene sorbitan tri- or monostearate. A preferred poloxamer is a block copolymer of ethylene oxide and propylene oxide having the following structure:

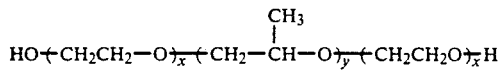

wherein x and y are positive integers and said copolymer comprises about 50 to 80 weight % polyethylene and has an average molecular weight of greater than 3,000, preferably between about 3,000 and about 15,000. Examples of such preferred poloxamers within the above-noted structure include Pluronic polyol F127 (molecular weight of about 12,000) and F68 (molecular weight of about 6,000) available from BASF Wyandotte Corporation. Another preferred O/W emulsifier is Tergitol XH (available from Union Carbide Corporation). Tergitol XH is a polyalkylene glycol ether of the formula:

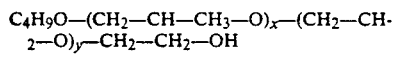

wherein x and y are positive integers and said glycol ether has an average molecular weight of about 3,500.

Both the O/W emulsifier and the W/O emulsifier are known in the art and can be made by known techniques and/or are commercially available.

The mixture of water and polymer solution is subjected to comminuting force in Step II by means of common devices such as homogenizers, colloid mills, ultrasonic vibrators, etc. It is usually desirable to bring the particle size distribution of emulsion droplets to a narrow range. The particle size reduction means used in Step III can be any particle size reduction means which achieves the desired droplet size. This task is preferably accomplished by passing the polymer solution-in-water emulsion through a Microfluidizer to achieve the particle size distribution in the range of about 0.1 to 0.8 $\mu$m, preferably about 0.1 to 0.5 $\mu$m.

The viscosity of the polymer solution-in-water emulsion formed in Step II is typically about 10 to about 50 centipoise (cps); preferably about 15 to about 25 cps. Viscosity can be measured by ASTM Procedure D2196.

Removal of the organic solvent in Step IV can be accomplished by any means known in the art. A convenient means for removing the organic solvent is by use of distillation methodology preferably under reduced pressure.

The drying of Step V can be accomplished by any drying means known in the art. Preferred is spray drying or freeze drying.

The present invention is also directed to a polymeric composition that can be produced by the above-described processes (i.e., after Step V). Such a powdered, polymeric composition comprises:

(A) about 42.5 to about 98 weight %, preferably about 75 to about 90 weight %, of at least one water insoluble polymer, (B) about 0.5 to about 30 weight %, preferably about 5 to about 15 weight %, of at least one oil-in-water emulsifier which is polymeric, water soluble or water dispersible and nonionic, (C) about 1 to about 27.5 weight %, preferably about 2 to about 10 weight %, of at least one water-in-oil emulsifier which is water insoluble; anionic or amphoteric; more hydrophobic than said oil-in-water emulsifier, said polymeric composition being in the form of particles having an average particle size of about 10 to 30 $\mu$m, preferably about 10 to 20 $\mu$m.

The polymeric, powdered composition can optionally contain about 5 to about 10 weight % of a medicament.

The present invention is also directed to a process for preparing a solid dosage form which comprises:

(A) dispersing the powdered, polymeric composition of the present invention in an aqueous solution which comprises at least about 85 weight % water to prepare a coating dope, and (B) coating a solid medicament core with the coating dope of step (A).

In the process for preparing a solid dosage form it is preferred that the aqueous solution further comprises up to 15 weight % of at least one coating additive, preferably about 10 to about 25 weight %, based on the total weight of aqueous solution.

Commonly used coating additives include plasticizers such as dimethyl phthalate, diethyl phthalate, dioctyl phthalate, a monoglyceride, or triacetin; water-soluble polymers; annealing agents; pharmaceutical clays; colorants; additional surfactants such as Tween 80; thickening agents; and the like. These can be directly added to the latex dispersion (i.e., dry powder), or to the aqueous suspension prepared by mixing a readily water-dispersible powder material in water, to form a coating dope for aqueous film-coating of pharmaceutical dosage forms.

If the coating polymers exhibit acidic or basic functional groups, it is especially preferred to add a small amount of bases or acids, appropriately, as annealing agents to the coating dopes to partially neutralize the respective coating polymers, while still maintaining the integrity of the colloidal dispersions, so as to enhance coalescing effect in the film-forming process on the surface of a substrate. A preferred amount of base is about 5% to about 50% equivalent of acid functional groups, and a preferred amount of acid is about 5% to about 50% equivalent of basic functional groups. Typical bases include hydroxides such as NH$_4$OH NaOH and KOH; typical acids include acetic acid and hydrochloric acid.

In addition to coating a medicament core, a suitable medicament which exhibits low solubility in water, but miscible or dispersible in a common solvent system for a selected polymer or blend of polymers can be incorporated in the first process Step I of either of the two processes first described in this detailed description.

If a medicament is added in Step I, a preferred concentration of medicament is about 10 to about 40 weight %, therefore, the complete, preferred process (after Step V) will yield either a medicament-loaded, latex-like colloidal dispersion, or, after drying, water-dispersible microparticle in powder form.

The "medicament" as used in the present invention is used in its broadest sense to include any active ingredient. Therefore, such active ingredients include typical medicaments used in the art such as aspirin, ibuprofen, ivermectin, efrotomycin, endomethacin, theophylline, propanolol, sucrose, erythromycin, UV absorbers, and the like.

In the method for treating animals the solid dosage form is preferably administered as a suppository or orally. Preferred is orally. The solid dosage form contains an effective amount of a medicament which is that amount typically used in the art to render a desired treatment. This amount will vary greatly depending upon the nature of the medicament and the desired type of treatment. "Treatment" refers to any desired purpose for administering a medicament such as prevention, control or cure of a disease; maintaining or improving the health of an animal; increasing weight gain or feed conversion of a farm animal; and the like.

In addition to being capable of forming a powdered, polymeric composition, the aqueous colloidal dispersion formed by Step IV can be used to prepare a cosmetic formulation such as a cream, suntan lotion, ointment and the like. Such a cosmetic formulation typically contains about 10 to about 25 weight % of said aqueous colloidal dispersion, preferably about 10 to about 20 weight %. Such a cosmetic formulation contains at least one active ingredient ("medicament") such as a UV absorber, for example, 2-hydroxy 4-methoxy benzophenone, octyl dimethyl para-amino benzoic acid or 2-ethylhexyl salicylate in amounts up to about 15 weight %, preferably about 4 to about 12 weight %. For suntan lotions, a preferred composition comprises from about 0.1 to about 1 weight %, preferably about 0.1 to about 0.5 weight % of a W/O emulsifier, preferably a mixture of phosphated mono- and di-glycerides such as Emphos D70-30C; about 0.2 to about 2 weight %, preferably about 0.5 weight %, of a O/W emulsifier, preferably a poloxamer such as Pluronic F-127; and about 50 to about 70 weight %, preferably about 60 weight % of water. It is more preferred that said cosmetic formulation, particularly said suntan lotion, contains up to about 40 weight % of at least one cosmetic additive, preferably about 20 to about 30 weight %. Such cosmetic additives include surfactants such as Tween 85, stearic acid, or hexanedecanol; preservatives such as glydant; fragrances such as lemon oil, orange oil; Vitamin E derivatives, such as Vitamin E succinate; propylene glycol; waxes such as Spermaceti wax; and the like.

All of the patents and other references cited in the present specification are incorporated herein by reference in their entirety.

The following examples illustrate the present invention but should not be interpreted as a limitation thereon.

EXAMPLE 1

This example illustrates the preparation of water-dispersible cellulose acetate phthalate (CAP) using the described process.

1. Dissolve 100 g of CAP (32%–36% phthalyl content) in 700 g of a solvent system consisting of ethylacetate/isopropanol (70/30 w/w). The amount of CAP constitutes 12.5% by weight of the solution.

2. Add to the CAP solution a system of food grade emulsifying agents consisting of an oil-in-water (O/W) emulsifier of nonionic nature and a water-in-oil (W/O) emulsifier of anionic nature which is dispersible in the organic phase and more hydrophobic than the nonionic surfactant.

Specifically, the emulsifying system is a poloxamer, Pluronic polyol F127, available from BASF Wyandotte Corporation, and phosphated mono-and diglyceride, Emphos D70-30C, available from Witco Company. The amount of Pluronic F127 is 14 g (14% of the polymer weight); the amount of Emphos D70-30C is 4 g (4% of the polymer weight).

3. Emulsify the CAP solution by slowly adding water to the organic phase while subjecting the mixture to the action of comminuting force so that a water-in-polymer solution (W/O) emulsion is initially formed, which upon further addition of a sufficient amount of water, inverts to form a stable polymer solution-in-water emulsion (O/W). The total amount of water is 900 g. A Ross homogenizer was used to generate the comminuting force. It is usually desirable, but not essential, to further bring the particle size of the (O/W) emulsion to a narrow distribution. This task can be accomplished by passing the polymer solution-in-water (O/W) emulsion through a Microfluidizer to reduce the particle size of the emulsion droplets. This process step was carried out at ambient temperature, and the highest temperature reading did not exceed 35° C. in the entire process step. The particle sizes and size distribution of emulsions were measured by using a Microtrac Small Particle Analyzer (Leeds and Northrup). Results are reported as the maximum particle size for a particular volume fraction of the total dispersed phase. Typical particle sizes of the (O/W) emulsions are:

| CAP (O/W) Emulsion Before Microfluidization | | CAP (O/W) Emulsion After Microfluidization |
|---|---|---|
| % Particle Volume | Max. Particle Size μm | Max. Particle Size, μm |
| 10% | 0.18 | 0.13 |
| 50% | 0.42 | 0.31 |
| 90% | 0.90 | 0.73 |

4. Remove the volatile organic solvents from the polymer solution-in-water emulsion by a distillation method under reduced pressure at 40°–50° C. such as employing a laboratory Rotavap to yield a latex-like colloidal dispersion. The polymer dispersion particle size after the removal of organic solvents essentially remain in the same range as the O/W emulsion. Typical particle sizes of the latex-like dispersion are:

| % Particle Volume | Max. Particle Size μm |
|---|---|
| 10% | 0.23 |
| 50% | 0.32 |
| 90% | 0.62 |

5. Spray-dry the polymer colloidal dispersion to yield a free flowing, readily water-dispersible powder (WD CAP).

Typical spray-drying conditions are given as follows:
Average Flow Rate: 50–60 mL/min.
Inlet Temperature: 110°–120° C.
Outlet Temperature: 60° C.
Average Air Feed Rate: 660 cubic ft/min.

The respective average maximum particle sizes of the finished products are in the range of 15–25 μm for 90% of the measured particles.

EXAMPLE 2

This example illustrates the need for incorporating an anionic surfactant such as phosphated mono- and diglycerides (Emphos) in the formulation to produce a stable, latex-like, CAP colloidal dispersion. In the absence of the anionic surfactant, the particle sizes of the suspension are much larger compared to the results given in Example 1.

The process steps as described in Example 1 were followed in the experiments in this example to prepare aqueous CAP colloidal dispersions. Ninety grams of CAP were dissolved in 453.3 g of ethylacetate/isopropanol (85/15 w/w). Ten grams of Pluronic Polyol F127 were then dissolved in the polymer solution. To the polymer solution which was subjected to constant agitation by using a Ross homogenizer, 583 g of water were added slowly at approximately 210 mL/min to yield an O/W emulsion. The emulsion was passed through a Microfluidizer, and then the solvent was evaporated to yield a colloidal suspension.

The particle sizes of the intermediates and the finished aqueous dispersion are given in the following table. These data indicates that in the absence of an anionic surfactant, the particle sizes of emulsion and the aqueous dispersion are much larger than the data given in Example 1. The aqueous dispersion also tends to settle in a short period of time.

EXAMPLE 2A

In this example, the anionic surfactant (Emphos D70-30C) is replaced with an amphoteric surfactant (lecithin) to prepare water-dispersible CAP.

This example illustrates the use of amphoteric emulsifier in the preparation of water-dispersible CAP using process in accordance with Example 1.

1. Dissolve 50 g of CAP in 350 g of a solvent system consisting of a mixture of ethyl acetate/isopropyl alcohol (75/25 by weight). Add 9.6 g Pluronic F-127 and 4.8 g of Lecithin to the CAP solution. Emulsify the polymer solution by slowly adding water to organic phase while subjecting the mixture to the vigorous agitation using Ross mixer, so that W/O emulsion is initially formed. Upon further addition of water (450 g) to the system, occurrence of phase inversion results in the formation of stable O/W emulsion. The typical particle sizes of the O/W emulsion are:

| % Relative Volume | Maximum Particle Size of o/w Emulsion (μm) |
|---|---|
| 10 | 0.18 |
| 50 | 0.42 |
| 90 | 0.83 |

2. In order to reduce particle size as well as being the particles of O/W emulsion to a narrow size distribution, the emulsion is passed through a Microfluidizer in accordance with Example 1. Typical particle sizes of O/W emulsion after microfluidization are:

| % Relative Volume | Maximum Particle Size of o/w Emulsion (μm) |
|---|---|
| 10 | 0.13 |
| 50 | 0.39 |
| 90 | 0.79 |

3. The volatile organic solvents are removed from the system to obtain an aqueous latex-like colloidal dispersions of CAP. Typical particle sizes of CAP dispersions in water are:

| % Relative Volume | Maximum Particle Size of o/w Emulsion (μm) |
|---|---|
| 10 | 0.13 |
| 50 | 0.43 |
| 90 | 0.85 |

EXAMPLE 3

This example shows the results of a series of experiments using various combinations of compositions and solvent systems to illustrate the preferred combinations.

| | Emulsion Before Microfluidization | Emulsion After Microfluidization | Dispersion After Removal of Solvent |
|---|---|---|---|
| % Particle Volume | Max. Particle Size μm | Max. Particle Size, μm | Max. Particle Size, μm |
| 10% | 0.43 | 0.21 | 3.45 |
| 50% | 0.90 | 0.44 | 7.10 |
| 90% | 2.33 | 0.90 | 12.45 |

| No. | CAP %, /w | Pluronic %, w/w | Emphos %, w/w | EA/IPA %, w/w | Solid % w/w | Particle Size (μm) 10% | 50% | 90% | Water/Sol. Ratio (w/w) |
| --- | --- | --- | --- | --- | --- | --- | --- | --- | --- |
| 1. | 80.0 | 7.0 | 13.0 | 65/35 | 6.0 | 0.20 | 0.54 | 1.59 | 1.286 |
| 2. | 90.0 | 2.0 | 8.0 | 65/35 | 8.8 | — | — | — | 1.286 |
| 3. | 80.0 | 15.0 | 5.0 | 65/35 | 8.8 | 0.23 | 0.62 | 1.42 | 1.286 |
| 4. | 90.0 | 10.0 | 0.0 | 65/35 | 6.0 | 0.20 | 0.51 | 1.82 | 1.286 |
| 5. | 80.0 | 7.0 | 13.0 | 85/15 | 8.8 | 0.20 | 0.42 | 0.92 | 1.286 |
| 6. | 90.0 | 2.0 | 8.0 | 85/15 | 6.0 | 0.43 | 1.23 | 3.16 | 1.286 |
| 7. | 80.0 | 15.0 | 5.0 | 85/15 | 6.0 | 0.13 | 0.29 | 0.64 | 1.286 |
| 8. | 90.0 | 10.0 | 0.0 | 85/15 | 8.8 | 3.45 | 7.10 | 12.45 | 1.286 |
| 9. | 85.0 | 8.5 | 6.5 | 75/25 | 7.4 | 0.13 | 0.36 | 0.73 | 1.286 |
| 10. | 85.0 | 8.5 | 6.5 | 75/25 | 7.4 | 0.13 | 0.35 | 0.84 | 1.286 |
| 11. | 87.3 | 11.8 | 0.9 | 75/25 | 7.4 | 0.21 | 0.50 | 0.90 | 1.286 |
| 12. | 53.4 | 11.9 | 34.7 | 75/25 | 7.4 | 0.73 | 0.20 | 4.14 | 1.286 |
| 13. | 56.8 | 39.8 | 3.4 | 75/25 | 7.4 | <0.12 | <0.12 | <0.12 | 1.286 |

Extensive precipitation was observed in Experiment 2. Detailed results of Experiment 8 are given in Example 2.

EXAMPLE 3A

Example 1 is repeated in detail with the exception that the Pluronic F127 used as one of the emulsifying agents is replaced with Tergitol XH. The ingredients employed in the preparation of water-dispersible CAP have the following compositions:
100 grams: CAP (32%-36% phthalyl content)
14 grams: Tergitol XH
4 grams: Emphos D70-30C
525 grams: Ethyl Acetate
175 grams: Isopropyl Alcohol
900 grams: Water The typical particle sizes of the O/W emulsion are:

| % Relative Volume | Particle Size (μm) Before Microfluidization | After Microfluidization | After Solvent Removal |
| --- | --- | --- | --- |
| 10 | 0.21 | 0.28 | 0.29 |
| 50 | 0.44 | 0.56 | 0.57 |
| 90 | 0.88 | 0.95 | 0.96 |

EXAMPLE 4

In this example, both cellulose acetate trimellitate (CAT), and CAP were used to illustrate the existance of phase inversion in the described process.

Fifty grams of CAT were dissolved in 350 g of a solvent system consisting of 70/30 or 80/20 (w/w) ethylacetate/isopropanol. Two grams of Emphos (D70-30C) and 7 g of Pluronic polyol (F-127) were then admixed to the polymer solution. A total amount of 450 g of water was added slowly to the polymer phase which was subjected to agitation by using a Ross homogenizer. The viscosity values of the system were measured by employing a Brookfield viscometer.

Results are shown as follows:

| Solvent System A Water/ (EA/IPA 70/30) Volume Ratio | Viscosity cps | Solvent System B Water/ (EA/IPA 80/20) Volume Ratio | Viscosity cps |
| --- | --- | --- | --- |
| 0.000 | 427 | 0.000 | 792 |
| 0.056 | 243 | 0.055 | 373 |
| 0.111 | 200 | 0.111 | 297 |
| 0.167 | 176 | 0.167 | 322 |
| 0.222 | 160 | 0.222 | 375 |
| 0.278 | 180 | 0.278 | 474 |
| 0.333 | 200 | 0.311 | 566 |
| 0.389 | 234 | 0.333 | 683 |
| 0.444 | 212 | 0.355 | 904 |
| 0.500 | 224 | 0.389 | 567 |
| 0.555 | 181 | 0.422 | 343 |
| 0.611 | 92 | 0.444 | 231 |
| 0.667 | 59 | 0.500 | 114 |
| 0.778 | 37 | 0.555 | 71 |
| 0.889 | 28 | 0.611 | 49 |
| 1.000 | 22 | 0.667 | 39 |
|  |  | 0.778 | 28 |
|  |  | 1.000 | 21 |

For the Solvent System A, a maximum viscosity peak occurred at the water/solvent ratio of 0.4 to 0.5; for the Solvent System B, the peak appeared at the ratio of 0.3 to 0.4. Similarly, two maximum viscosity peaks were observed at the water to solvent (EA/IPA 80/20) ratios of 0.25 and 0.6 in the process for CAP solution-in-water emulsion. These results indicate phase inversion in the described process.

EXAMPLE 5

This example illustrates the importance of phase inversion in the disclosed process.

CAT or CAP solution (350 g each) as given in Example 4 was added to 450 g of water with vigorous mixing. Both operations failed to produce a stable emulsion. Two distinctive layers with a lot of foams on the top layer (polymer phase) were observed.

EXAMPLE 6

This example illustrates the use of water-dispersible CAP prepared as described in Example 1, for coating solid dosage forms.

1. Dissolve 20 g of each triacetin and dimethyl phthalate (DMP) used as plasticizers in 782.5 g of distilled water containing 0.5 g of Tween 80. Add 100 g of water dispersible cellulose acetate phthalate (WD CAP) to the aqueous solution of plasticizers using a magnetic stirrer for obtaining a hydroxide (annealing agent) (6 g 30% aqueous solution) was added to the coating dope. After 10 min of additional stirring, the coating suspension is ready for application to solid dosage forms.

2. The coating dope prepared from CAP pseudolatex was employed for coating of aspirin tablets. The coating was performed by spraying the dope on tablets in a pan coater (Freund Model HCT-30, HI Coater). Typical operating conditions used for water-borne coating were:

| Parameters | Operating Conditions |
|---|---|
| Batch Size | 1 (kg) |
| Pan Revolution | 12–15 (rpm) |
| Preheating and Dusting Time | 4–8 (min) |
| Drying Air Temperature | 75–85 (°C.) |
| Spraying Air Pressure | 18–22 (kg/cm$^2$) |
| Spraying Solution Feed | 3–10 (mL/min) |
| Solid Content in Spraying Solution | 14–18 (% wt) |
| Exhaust Air | 40–45 (°C.) |
| Final Drying Time | 15–20 (min) |
| Coating Weight | 5–10 (% wt) |

The coating was completed without any problem such as blocking of spray gun, tablet stickiness, etc., during the process. Coated tablets were good, glossy and elegent in appearance. For enteric protection, the U.S.P. enteric test was conducted to assess the enteric efficiency of the coated aspirin tablets. About 100 tablets were examined in a disintegration tester for 3 to 4 hours using simulated gastric buffer (pH=1.2) containing NaCl and HCl in water as the test medium at 37° C. Subsequently, the disintegration time in simulated intestinal buffer (pH=6.8) containing $KH_2PO_4$ and NaOH in water as the test medium was also evaluated at 37° C. Results demonstrated an ability to resist breakdown of coated enteric film in simulated gastric buffer for the period of 3 to 4 hours with only a 0.1% to 1.0% penetration of aspirin through the coating film, whereas the disintegration time in simulated intestinal buffer was 8 to 15 minutes. The disintegration time for uncoated tablets in intestinal buffer was 1 to 2 minutes.

EXAMPLE 7

A coating dope was made in accordance with Example 6, except that 3 g of $NH_4OH$ (30% ammonia in water) were used instead of 6 g of the same concentration. This coating formulation also applied to tablets, beads and pellets of different sizes, as well as to solid dosage forms containing different active ingredients such as sucrose, ibuprofen, aspirin, erythromycin and propranolol. The film formed on the solid dosage form was continuous, smooth and elegant. For enteric protection, the U.S.P. enteric test was performed as described in Example 6. Results obtained using disintegration tester indicated an ability to resist breakdown of the coated film in simulated gastric juice for 3–4 hours with only a 0.1% to 1.0% release of an active material from the coated solid dosage form, while the disintegration time in simulated intestinal buffer was 8 to 15 minutes and meet the U.S.P. enteric protection test.

EXAMPLE 8

Examples 6 and 7 are repeated with the exception that the coating dope is prepared without $NH_4OH$ and has the following composition:
100 grams: WD CAP
20 grams: Triacetin
20 grams: Dimethyl Phthalate
782.5 grams: Deionized Water Twenty grams of triacetin was mixed in 782.5 g of water using a magnetic stirrer. After complete mixing, 20 g of dimethyl phthalate was added to the solution while continuously stirring. Using a high speed agitator, 100 g of WD CAP was dispersed by adding slowly to the aqueous solution containing triacetin and dimethyl phthalate. After 2 to 3 hours of additional stirring using a magnetic stirrer, the suspension is ready for film coating. For color coating, a selected colorant is added to the coating suspension while stirring 10 minutes before starting the coating processes.

The coating was conducted in accordance with Example 6. The film formed on tablets, caplets and beads was continuous, elegant and smooth. In order to assess the enteric protection, the U.S.P. enteric test was conducted as stated in Example 6. Results demonstrated an ability to resist breakdown of the coated enteric film in simulated gastric juice for 3 to 4 hours with only less than 1.0% release of an active material from the coated solid dosage form, whereas the disintegration time in simulated intestinal fluid was 9 to 14 minutes.

EXAMPLE 9

Example 6 is repeated in detail with the exception that the dimethyl phthalate used as one of the plasticizers is replaced with diethyl phthalate. The coating dope has the following composition:
100 grams: WD CAP
20 grams: Diethyl Phthalate
10 grams: Triacetin
6 grams: $NH_4OH$ (30% Solution)
0.5 grams: Tween 80
782.5 grams: Water The coating dope was prepared as described in Example 5. Coated aspirin tablets did not dissolve in simulated gastric buffer for 3 hours, and released active material in simulated intestinal buffer in 9 to 12 minutes.

EXAMPLE 10

Example 9 was repeated with the exception that 3.0 g of $NH_4OH$ (30% solution in water) were used instead of 6.0 g of the same concentration in the coating dope.

EXAMPLE 11

This example illustrates the incorporation of UV-absorber in an aqueous dispersion of CAP.

1. 50 g of CAP (32% to 36% phthalyl content) was added to 350 g of an 80 to 20 weight ratio of ethyl acetate - isopropanol solvent system with constant stirring. The resultant CAP solution was filtered, and 10 g of 2-hydroxy 4-methoxy benzophenone used as a UV-absorber was added. After complete mixing, 9.8 g of Pluronic F-127 and 4.9 g of Emphos D70-30C were added in the manner set forth in Example 1.

2. The resultant polymer solution was emulsified by adding deionized water in accordance with Example 1. Typical particle size of the dispersions in the presence and in the absence of solvent are:

| % Relative Volume | Particle Size of Dispersions ($\mu$m) | |
|---|---|---|
| | Before Solvent Removal | After Solvent Removal |
| 10 | 0.35 | 0.37 |
| 50 | 0.82 | 0.87 |
| 90 | 1.88 | 2.03 |

A typical ingredient composition of an aqueous, colloidal dispersion of UV absorber incorporated microparticles is:

| Ingredients | Weight (%) |
|---|---|
| CAP | 9.53 |
| Pluronic F-127 | 1.87 |
| Emphos D70-30C | 0.93 |
| 2-hydroxy-4-methoxy benzophenone | 1.91 |
| Water | 85.76 |

EXAMPLE 12

In this example, the UV-absorber incorporated colloidal aqueous polymeric dispersions prepared in accordance with Example 11 were used to form suntan lotion.

The process employed in the formulation of suntan lotion is divided in two parts. The first part contains 1.93 g of Spermaceti, 0.65 g of Myverol 18-06 (a monoglyceride), 0.50 g of stearic acid, 0.50 g of propylene glycol, 0.08 g of hexadecanol and 0.16 g of vitamin E succinate, while the second part includes aqueous polymeric dispersions as prepared in Example 11. To the UV-absorber incorporated polymer dispersions in water, 0.015 g of Tween 85 was added. The ingredients of first part were melted together by gentle mixing and heating to 60° C. The aqueous polymer dispersions (second part) was heated to 60° C., and melted ingredients of first part were added slowly while subjecting the mixture to the gentle stirring. The entire mixture was stirred until cool. After cooling, preservatives and fragrances were added during stirring to the mixture. The resultant suntan lotion has the following composition:

| Ingredients | Weight (%) |
|---|---|
| Water dispersible CAP | 11.02 |
| 2-Hydroxy-4-Methoxy Benzophenone (UV-Absorber) | 1.73 |
| Water | 66.41 |
| Tween 85 | 0.11 |
| Spermaceti | 10.42 |
| Myverol 18-06 | 3.51 |
| Stearic Acid | 2.70 |
| Propylene Glycol | 2.70 |
| Hexadecanol | 0.43 |
| Vitamin E Succinate | 0.86 |
| Glydant (Preservative) | 0.11 |

The lotion forms a thin and smooth film, and film does not feel gritty due to the compatibility and small particle size of polymer dispersions.

EXAMPLE 13

This example describes the preparation of water-dispersible 2-vinylpyridine/styrene (2VP/ST) using process in accordance with Example 1.

1. Dissolve 20 g of 2VP/ST (mol. wt.=600,000) in 400 g of a solvent system consisting of a mixture of ethyl acetate/isopropanol (90/10 wt/wt). The amount of 2VP/ST polymer constitutes 5% by weight of the solvent.

2. Add 7.0 g of Pluronic F127 and 1 g of Emphos D70-30C to the 2-vinylpyridine/styrene solution. Emulsify the polymer solution by slowly adding water to the organic phase while subjecting the mixture to the vigorous agitation, so that water-in-oil emulsion is intially formed. Upon further addition of water (850 g) to the system, occurrence of phase inversion results in the formation of stable oil-in-water emulsion. A Ross homogenizer was used to generate the vigorous agitation.

The typical particle sizes of the oil-in-water emulsion are:

| % Relative Volume | Maximum Particle Size of 2VP/ST (O/W) Emulsion, (μm) |
|---|---|
| 10 | 0.55 |
| 50 | 1.70 |
| 90 | 4.57 |

3. In order to enhance the quality of the final product, it is desirable to further reduce the particle size, as well as bring the particles of O/W emulsion to a narrow size distribution. This task was achieved by passing the emulsion system through a Microfluidizer in accordance with Example 1. Typical particle sizes of O/W emulsion after microfluidization are:

| % Relative Volume | Maximum Particle Size of (O/W) Emulsion, (μm) |
|---|---|
| 10 | 0.44 |
| 50 | 0.98 |
| 90 | 2.64 |

4. The volatile organic solvents are removed from the system as described in Example 1. Typical particle sizes of 2VP/ST dispersion in water are:

| % Relative Volume | Maximum Particle Size of 2VP/ST Dispersions in Water (μm) |
|---|---|
| 10 | 0.41 |
| 50 | 0.86 |
| 90 | 2.25 |

These results indicate that the size of 2VP/ST dispersions is larger than that of CAP dispersions in water which may be due to large molecular weight of 2VP/ST polymer used to form these dispersions.

EXAMPLE 14

This example illustrates the incorporation of efrotomycin in polymer particles for post-ruminal drug delivery.

1. Dissolve 20 g of 2VP/ST (mol. wt. ~600,000) in 400 g of a mixture of ethyl acetate/isopropanol (90/10 wt/wt). Add 4 g of efrotomycin to the polymer solution while subjecting the system to vigorous agitation. After complete mixing, 7 g of Pluronic F127 and 1 g of Emphos D70-30C were added to the system, and a homogeneous solution was prepared by gentle mixing.

2. The resultant polymer solution was emulsified by adding deionized water slowly to the system while subjecting the mixture to vigorous agitation. A water-in-oil emulsion was formed initially, whereas upon further addition of water, phase inversion occurs, and oil-in-water emulsion is formed. Typical particle sizes of efrotomycin-bound 2VP/ST dispersions are:

| % Relative Volume | Maximum Particle Size in μm |
|---|---|
| 10 | 0.56 |
| 50 | 1.67 |
| 90 | 5.03 |

3. In order to improve the quality and stability of the drug-bound polymeric dispersions, it is desirable, but not essential, to further bring the particle size distribution to a narrow range by passing dispersions through a Microfluidizer. Typical particle sizes of the dispersions are:

| % Relative Volume | Maximum Particle Size in μm |
|---|---|
| 10 | 0.39 |
| 50 | 0.76 |
| 90 | 1.65 |

These results indicate that the presence of efrotomycin in forming 2VP/ST aqueous, colloidal, dispersions produces polymeric particles with smaller sizes as compared with the particles produced in the absence of efrotomycin (Example 13).

4. Protection of an aqueous suspension of efrotomycin-2VP/ST was determined by examining biological activity of drug. For biological activity studies, one year old samples of efrotomycin-2VP/ST aqueous, collloidal suspension were evaluated by measuring in vitro growth of aerobic and anaerobic bacteria.

For aerobic bacterial growth, several stainless steel cylinders were placed on top of a nutrient agar plate containing a homogeneous top layer of agar-*Bacillus megaterium*. The efrotomycin-2VP/ST aqueous suspension was extracted in simulated rumen fluid (pH=5.4) for 24 hours using shaking water bath at 39° C. To each cylinder, 100 μL of centrifuged extract was added, and plates were incubated for 24 hours at 37° C. Protection was determined by measuring the zone diameter of growth inhibition around the cylinders. Results indicated that the protection was approximately 83% as compared to bulk drug. In addition, HPLC analysis also showed that 90% efrotomycin was present in an aqueous suspension of efrotomycin-2VP/ST after one year of storage.

The protection of efrotomycin was also examined by correlating growth of anaerobic bacteria with consumption of carbohydrate from anaerobically prepared liquid growth medium of pH 5.4 containing centrifuged rumen fluid. An appropriate amount of efrotomycin-2VP/ST dispersions containing drug in the range of 32 to 1,368 μg/mL was taken in the culture tubes. Three milliliter of culture medium was added to the test sample, and then 20 μL active *Streptococcus bovis* JB1 was added. These culture tubes were incubated for 24 hours at 39° C. The carbohydrate content in the broth was analyzed spectrophotometrically. Complete carbohydrate usage indicates 100% relative growth. The inhibition of growth of the rumen bacteria, *Streptococcus bovis* JB1, method showed a better than 74.7% protection of efrotomycin drug in efrotomycin-2VP/ST aqueous dispersions.

5. In vitro studies to assess the biological activity of the released efrotomycin from the 2VP/ST-efrotomycin aqueous dispersion were investigated aerobically with *B. megaterium*. A sample of the aqueous disperion was extracted in pH 2.9 citrate-phosphate buffer that 45 minutes using a shaking water bath at 39° C. Bovine bile was added to the flask containing extracted sample, and placed in the water bath for additional extraction (40 minutes). After 1.5 hours, the pH of the extracting sample was adjusted to 7.0 with a NaOH solution. Samples were removed from the test flask after 1, 2 and 5 hours. As a control, bulk drug was treated in the same manner as the aqueous dispersion. During the extraction period, all aliquots were removed at different time intervals as indicated above, and were centrifuged immediately. The centrifuged extracts were tested for biological activity of efrotomycin by the microbiological cylinder plate assay as described in this example (Section 4). Release of efrotomycin from the 2VP/ST-efrotomycin suspension, and biological activity of the released antibiotic were determined by measuring the diameter of the zone of bacterial growth inhibition around the cylinder. Experimental data are as follows:

| Time (Hour) | pH | Zone of Growth Inhibition (mm)* | |
|---|---|---|---|
| | | Bulk Drug | 2VP/ST-Efrotomycin Aqueous Dispersion |
| 0.75 | 2.9 | 16.0 | 15.7 |
| 1.40 | 2.9 | 14.8 | 14.4 |
| 2.40 | 7.0 | 14.0 | 13.4 |
| 4.40 | 7.0 | 13.2 | 13.0 |
| 6.40 | 7.0 | 10.9 | 10.4 |

*Biological activity of efrotomycin is represented as the measure of a growth inhibition zone. The zone diameter greater than 8 mm shows biological activity.

Results showed that efrotomycin was released, and the biological activity of efrotomycin in the aqueous dispersion was maintained as that of the bulk drug for a total time period of 6.4 hours of extraction, which includes sample extraction in simulated abomasal buffer (pH=2.9) for 1.5 hours and extraction up to 5 hours in simulated intestinal buffer (pH=7.0).

EXAMPLE 15

In this example, the efrotomycin-bound 2-vinylpyridine/styrene powder (e.g. pseudolatex) was formed by removing water from the system. This task can be accomplished by spray or freeze drying of aqueous efrotomycin-bound polymer dispersions prepared in the manner set forth in Example 14. The polymeric dispersions were spray dried in accordance with Example 1. Typical particle size of spray dried efrotomycin-bound 2VP/ST particles is in the range of 5 to 40 μm, with an average size nearly 15 μm.

The protection and biological activity of efrotomycin in drug-bound 2VP/ST powder was evaluated in the manner set forth in Example 14. Results indicated that the efrotomycin protection was nearly 83% in pseudolatex as compared to bulk drug. In addition, HPLC analysis showed that 90% efrotomycin was protected in pseudolatex formulation after one year of storage at room temperature. Experimental results of anaerobic bacterial growth studies also indicated that 95.4% efrotomycin was protected in pseudolatex formulation.

In vitro studies to assess the biological activity of the released efrotomycin from the efrotomycin-bound 2VP/ST powder were measured as described in Example 14 (Section 5). Typical data of biological activity and release are:

| Time (Hour) | pH | Zone of Growth Inhibition (mm)* | |
|---|---|---|---|
| | | Bulk Drug | 2VP/ST-Efrotomycin Powder |
| 0.75 | 2.9 | 16.0 | 16.3 |
| 1.40 | 2.9 | 14.8 | 14.8 |
| 2.40 | 7.0 | 14.0 | 13.4 |
| 4.40 | 7.0 | 13.2 | 12.2 |
| 6.40 | 7.0 | 10.9 | 10.4 |

*Biological activity of efrotomycin is represented as the measure of a growth inhibition zone. The zone diameter greater than 8 mm shows biological activity.

Experimental results demonstrated that efrotomycin was released, and the biological activity was maintained as that of the bulk drug for a total time period of 6.4 hours of extraction, which includes sample extraction in simulated abomasal buffer (pH=2.9) for 1.5 hours and extraction up to 5 hours in simulated intestinal buffer (pH=7.0).

EXAMPLE 16

Example 14 was repeated with the exception that Ivermectin was incorporated instead of efrotomycin the 2-vinylpyridine/styrene dispersions.

1. Dissolve 20 g of 2 VP/ST in a solvent system containing mixture of ethyl acetate and isopropanol (90:10 wt/wt). A 1.5 g of Ivermectin sample was dissolved in polymer solution by gentle mixing. After complete mixing, 7.0 g of Pluronic F127 and 1.0 g of Emphos D70-30C were added to the system in the presence of vigorous agitation.

2. The resultant polymer solution was emulsified in the manner set forth in Example 14. Typical particle size of Ivermectin-bound polymer is:

| % Relative Volume | Maximum Particle Size in μm |
|---|---|
| 10 | 0.55 |
| 50 | 1.59 |
| 90 | 4.81 |

The particle size and size distribution of Ivermectin-bound polymeric dispersions are further reduced by using a Microfluidizer as described in Example 14. Typical particle size of dispersions is:

| % Relative Volume | Maximum Particle Size in μm |
|---|---|
| 10 | 0.37 |
| 50 | 0.67 |
| 90 | 1.41 |

After removing solvents from the system, the particle size of aqueous dispersions remains in the same range (e.g., 0.3 to 1.5 μm), whereas after spray drying, the particle size of the powder is in the range of 5 to 40 μm with an average size approximately 15 μm.

We claim:

1. A polymeric composition comprising
   (A) about 42.5 to about 98 weight % of at least one water insoluble polymer,
   (B) about 0.5 to about 30 weight % of at least one oil-in-water emulsifier which is polymeric, water soluble or water dispersible and nonionic.
   (C) about 1 to about 27.5 weight % of at least one water-in-oil emulsifier which is water insoluble; anionic or amphoteric; more hydrophobic than said oil-in-water emulsifier; substantially dispersible in a low molecular weight, more volatile than water, and substantially water immiscible organic solvent; and compatible with said oil-in-water emulsifier, said polymeric composition being in the form of particles having an average particle size of about 0.1–0.8 μm.

2. The composition of claim 1 wherein said water insoluble polymer is a pH-dependent acidic enteric cellulose polymer, a neutral cellulose ester, a pH-dependent basic cellulosic polymer, a pH-dependent polyvinylpyridine derivative, a pH-dependent polystyrene derivative, a pH-dependent styrene/vinylpyridine copolymer, a maleic anhydride copolymer, an acrylic/acrylate copolymer, an acrylic ester, a lactic/glycolic acid copolymer, a polyester or a polypeptide.

3. The composition of claim 1 wherein said oil-in-water emulsifier has a HLB value of greater than or equal to about 10.

4. The composition of claim 1 wherein said oil-in-water emulsifier is a poloxamer, polyoxyethylene sorbitan monolaurate, polyoxyethylene sorbitan tristearate, polyoxyethylene sorbitan monostearate, or a mixture thereof; said water-in-oil emulsifier is a phosphated monoglyceride, a phosphated diglyceride, a citric acid ester of a monoglyceride, a sodium stearoyl lactylate, a calcium stearoyl lactylate, glycerol monooleate, a diacetylated tartaric acid ester of a monoglyceride, a sulfonated ester, alpha-tocopherol hemisuccinate, a soy phosphatide, a phospholipid, a lysophospholipid, or a mixture thereof; and wherein said water insoluble polymer is cellulose acetate phthalate, cellulose acetate trimellitate, cellulose acetate succinate, cellulose acetate propionate phthalate, hydroxypropyl methyl cellulose phthalate, cellulose acetate butyrate, cellulose acetate propionate, ethyl cellulose, cellulose propionate morpholinobutyrate, cellulose acetate diethylaminohydroxypropyl ether, diethylaminomethyl cellulose, 1-piperidyl-ethyl-hydroxyethylcellulose, benzylamino-ethylhydroxy-ethylcellulose, cellulose acetate, diethylaminoacetate, poly(2-vinylpyridine), poly(4-vinylpyridine), poly(2-vinyl-5-ethylpyridine), copoly(2-vinylpyridine/styrene), copoly(2-methyl-5-vinylpyridine/styrene) imidazoline modified copoly(styrene-acrylonitrile), dimethylaminoethyl modified polystyrene, poly(methyl vinyl ether/maleic anhydride), poly(ethylene maleic anhydride), poly(styrene/maleic anhydride), a ethylacrylate/methyl methacrylate copolymer, poly(ethylene terephthalate) or a mixture thereof.

5. The composition of claim 3 wherein said oil-in-water emulsifier is a block copolymer of the formula:

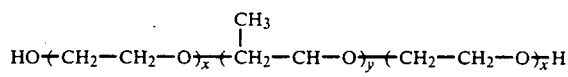

wherein x and y are positive integers and said copolymer has about 50 to 80 weight % polyethylene and has an average molecular weight of greater than 3,000, or a polyalkylene glycol ether of the formula:

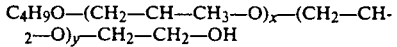

wherein x and y are positive integers and said glycol ether has a molecular weight of about 3,500; and said water-in-oil emulsifier is lecithin or a mixture of phosphated mono- and di-glycerides.

6. A product of a process comprising:
   (I) contacting
      (A) an organic solvent system comprising:
         (a) at least one water insoluble polymer, and
         (b) at least one low molecular weight, more volatile than water, and substantially water-immiscible organic solvent,
      with
      (B) a combination of surfactants comprising:
         (i) at least one oil-in-water emulsifier which is polymeric, water soluble or water dispersible, and nonionic, and (ii) at least one water-in-oil emulsifier which is water insoluble, anionic or amphoteric, more hydrophobic than said oil-in-water emulsifier, substantially dispersible in said organic solvent system, and compatible with said oil-in-water emulsifier, to result in an organic phase, (II) emulsifying said organic phase by adding sufficient water to said organic phase while subjecting the resulting mixture to comminuting force to form a water-in-polymer solution emulsion; and adding to said water-in-polymer solution emulsion an additional amount of water effective to result in a phase inversion to form a polymer solution-in-water emulsion, (III) passing the polymer solution-in-water emulsion through a microfluidizer such that the water insoluble polymer is in the form of droplets having an average size in range of about 0.1 to 0.8 $\mu$m, (IV) removing the organic solvent from the polymer-in-water solution emulsion to form an aqueous colloidal dispersion of polymer, and (V) drying the aqueous colloidal dispersion of polymer to form a water-dispersible powder, wherein, Component (A) comprises about 5 to about 35 weight % of Component (A)(a) and about 95 to about 65 weight % of Component (A)(b), based on the total weight of (A)(a) plus (A)(b); and Component (B)(i) is present in an amount of about 0.5% to about 70% of the weight of Component (A)(a), and Component (B)(ii) is present in an amount of about 1% to about 65% of the weight of Component (A)(a).

7. The product of claim 6 wherein for said process Component (A) comprises about 10 to about 30 weight % of Component (A)(a) and about 90 to about 70 weight % of Component (A)(b), based on the total weight of (A)(a) plus (A)(b); and Component (B)(i) is present in an amount of about 10% to about 50% of the weight of Component (A)(a), and Component (B)(ii) is present in an amount of about 2% to about 40% of the weight of Component (A)(a);

said organic solvent is methylene chloride, ethylene dichloride, chloroform, or isopropanol plus ethyl acetate;

said water insoluble polymer is cellulose acetate phthalate, cellulose acetate trimellitate, cellulose acetate succinate, cellulose acetate propionate phthalate, hydroxypropyl methyl cellulose phthalate, cellulose acetate, cellulose acetate butyrate, cellulose acetate propionate, ethyl cellulose, cellulose propionate morpholinobutyrate, cellulose acetate diethylaminohydroxypropyl ether, diethylaminomethyl cellulose, 1-piperidyl-ethylhydroxyethylcellulose, benzylaminoethylhydroxyethylcellulose, acetate diethylaminoacetate, cellulose poly(2-vinylpyridine), poly(4-vinylpyridine), poly(2-vinyl-5-ethylpyridine), copoly(2-vinylpyridine/styrene), copoly(2-methyl-5-vinylpyridine/styrene) imidazoline modified copoly(styrene-acrylonitrile), dimethylaminoethyl modified polystyrene, poly(methyl vinyl ether/maleic anhydride), poly(ethylene/maleic anhydride), poly(styrene/maleic anhydride), a ethylacrylate/methyl methacrylate copolymer, poly(ethylene terephthalate) or a mixture thereof;

said oil-in-water emulsifier is a poloxamer, polyoxyethylene sorbitan monolaurate, polyoxyethylene sorbitan tristearate, polyoxyethylene sorbitan monostearate, or a mixture thereof;

said water-in-oil emulsifier is a phosphated monoglyceride, a phosphated diglyceride, a citric acid ester of a monoglyceride, a sodium stearoyl lactylate, a calcium stearoyl lactylate, glycerol monooleate, a diacetylated tartaric acid ester of a monoglyceride, a sulfonated ester, alpha-tocopherol hemisuccinate, a soy phosphatide, a phospholipid, a lysophospholipid, or a mixture thereof; and the powder is in the form of particles having an average size of about 15 to 30 $\mu$m.

8. A product of a process comprising:

(I) contacting (A) an organic solvent system comprising:

(a) at least one water insoluble polymer, and (b) at least one low molecular weight, more volatile than water, and substantially water-immiscible organic solvent, with (B) at least one water-in-oil emulsifier which is water insoluble, anionic or amphoteric, and substantially dispersible in said organic solvent system, to result in an organic phase, and (II) emulsifying said organic phase by adding sufficient water to said organic phase while subjecting the resulting mixture to a comminnuting force to form a water-in-polymer solution emulsion; and adding to said water-in-polymer solution emulsion an additional amount of water effective to result in a phase conversion to form a polymer solution-in-water emulsion, wherein, said water contains at least one oil-in-water emulsifier which is polymeric, water soluble or water dispersible, nonionic, less hydrophobic than said water-in-oil emulsifier, and compatible with said water-in-oil emulsifier, (III) passing the polymer solution-in-water emulsion through a particle size reduction means such that the water insoluble polymer is in the form of droplets having an average size in the range of about 0.1 to 0.8 $\mu$m, (IV) removing the organic solvent from the polymer solution-in-water emulsion to form an aqueous colloidal dispersion of polymer, and (V) drying the aqueous colloidal dispersion of polymer to form a water-dispersible powder, wherein, Component (A) comprises about 5 to about 35 weight % of Component (A)(a) and about 95 to about 65 weight % of Component (A)(b), based on the total weight of (A)(a) plus (A)(b); and said oil-in-water emulsifier is present in an amount of about 0.5% to about 70% of the weight of Component (A)(a), and said water-in-oil emulsifier is present in an amount of about 1% to about 65% of the weight of Component (A)(a).

9. The product of claim 8 wherein for said process Component (A) comprises about 10 to about 30 weight % of Component (A)(a) and about 90 to about 70 weight % of Component (A)(b), based on the total weight of (A)(a) plus (A)(b); and said oil-in-water emulsifier is present in an amount of about 10% to about 50% of the weight of Component (A)(a), and said water-in-oil emulsifier is present in an amount of about 2% to about 40% of the weight of Component (A)(a);

said organic solvent is methylene chloride, ethylene dichloride, chloroform, or isopropanol plus ethyl acetate;

said water insoluble polymer is cellulose acetate phthalate, cellulose acetate trimellitate, cellulose acetate succinate, cellulose acetate propionate phthalate, hydroxypropyl methyl cellulose phthalate, cellulose acetate, cellulose acetate butyrate, cellulose acetate propionate, ethyl cellulose, cellulose propionate morpholinobutyrate, cellulose acetate diethylaminohydroxypropyl ether, diethylaminomethyl cellulose, 1-piperidyl-ethylhydroxyethylcellulose, benzylamino-ethylhydroxy-ethylcellulose, cellulose acetate, diethylaminoacetate, poly(2-vinylpyridine), poly(4-vinylpyridine), poly(2-vinyl-5-ethylpyridine), copoly(2-vinylpyridine/styrene), copoly(2-methyl-5-vinylpyridine/styrene) imidazoline modified copoly(styrene-acrylonitrile), dimethylaminoethyl modified polystyrene, poly(methyl vinyl ether/maleic anhydride), poly(ethylene/maleic anhydride), poly(styrene/maleic anhydride), a ethylacrylate/methyl methacrylate copolymer, poly(ethylene terephthalate) or a mixture thereof;

said oil-in-water emulsifier is a poloxamer, polyoxyethylene sorbitan monolaurate, polyoxyethylene sorbitan tristearate, polyoxyethylene sorbitan monostearate, or a mixture thereof;

said water-in-oil emulsifier is a phosphated monoglyceride, a phosphated diglyceride, a citric acid ester of a monoglyceride, a sodium stearoyl lactylate, a calcium stearoyl lactylate, glycerol monooleate, a diacetylated tartaric acid ester of a monoglyceride, a sulfonated ester, alpha-tocopherol hemisuccinate, a soy phosphatide, a phospholipid, a lysophosopholipid, or a mixture thereof; and the powder is in the form of particles having an average size of about 15–30 μm.

10. A process for preparing a solid dosage form comprising:
(A) dispersing the polymeric composition of claim 1 in an aqueous solution which comprises at least about 85 weight % water to prepare a coating dope, and
(B) coating a solid medicament core with the coating dope of step (A).

11. The process of claim 10 wherein said aqueous solution further comprises up to about 40 weight % of at least one coating additive.

12. The process of claim 11 wherein said coating additive is a plasticizer selected from the group consisting of dimethyl phthalate, diethyl phthalate, triacetin, and a mixture thereof.

13. The process of claim 11 wherein said coating additive is a surfactant.

14. The process of claim 11 wherein said coating additive is dimethyl phthalate, triacetin, diethyl phthalate, dioctyl phthalate, or a monoglyceride.

15. The process of claim 10 wherein said coating is carried out by spraying said cores with said coating dope in a pan coater.

16. A process for preparing a solid dosage form comprising:
(A) dispersing the polymeric composition of claim 2 in an aqueous solution which comprises at least about 85 weight % water to prepare a coating dope, and
(B) coating a solid medicament core with the coating dope of step (A).

17. A process for preparing a solid dosage form comprising:
(A) dispersing the polymeric composition of claim 3 in an aqueous solution which comprises at least about 85 weight % water to prepare a coating dope, and
(B) coating a solid medicament core with the coating dope of step (A).

18. A process for preparing a solid dosage form comprising:
(A) dispersing the polymeric composition of claim 4 in an aqueous solution which comprises at least about 85 weight % water to prepare a coating dope, and
(B) coating a solid medicament core with the coating dope of step (A).

19. A process for preparing a solid dosage form comprising:
(A) dispersing the polymeric composition of claim 5 in an aqueous solution which comprises at least about 85 weight % water to prepare a coating dope, and
(B) coating a solid medicament core with the coating dope of step (A).

20. A process for preparing a solid dosage form comprising:
(A) dispersing the polymeric composition of claim 6 in an aqueous solution which comprises at least about 85 weight % water to prepare a coating dope, and
(B) coating a solid medicament core with the coating dope of step (A).

21. A process for preparing a solid dosage form comprising:
(A) dispersing the polymeric composition of claim 7 in an aqueous solution which comprises at least about 85 weight % water to prepare a coating dope, and
(B) coating a solid medicament core with the coating dope of step (A).

22. A process for preparing a solid dosage form comprising:
(A) dispersing the polymeric composition of claim 8 in an aqueous solution which comprises at least about 85 weight % water to prepare a coating dope, and
(B) coating a solid medicament core with the coating dope of step (A).

23. A process for preparing a solid dosage form comprising:
(A) dispersing the polymeric composition of claim 9 in an aqueous solution which comprises at least about 85 weight % water to prepare a coating dope, and
(B) coating a solid medicament core with the coating dope of step (A).

24. A solid dosage form comprises an effective amount of a medicament coated with the polymeric composition of claim 1.

25. The solid dosage form of claim 24 wherein said medicament is present in an amount of about 96 to about 75 weight %; and said polymeric composition is present in an amount of about 4 to about 25 weight %.

26. A solid dosage form comprising an effective amount of a medicament coated with the polymeric composition of claim 2.

27. A solid dosage form comprising an effective amount of a medicament coated with the polymeric composition of claim 3.

28. A solid dosage form comprising an effective amount of a medicament coated with the polymeric composition of claim 4.

29. A solid dosage form comprising an effective amount of a medicament coated with the polymeric composition of claim 5.

30. A solid dosage form comprising an effective amount of a medicament coated with the polymeric composition of claim 6.

31. A solid dosage form comprising an effective amount of a medicament coated with the polymeric composition of claim 7.

32. A solid dosage form comprising an effective amount of a medicament coated with the polymeric composition of claim 8.

33. A solid dosage form comprising an effective amount of a medicament coated with the polymeric composition of claim 9.

34. The solid dosage form of claim 24 wherein said medicament is aspirin, ibuprofen, erythromycin, theophylline, propanolol, endomethacin sucrose or a mixture thereof.

35. A method for treating animals in need of treatment comprising orally administering to said animals the solid dosage form of claim 24, wherein the effective amount of medicament is an amount to render said treatment.

36. A method for treating animals in need of treatment comprising orally administering to said animals the solid dosage form of claim 25, wherein the effective amount of medicament is an amount to render said treatment.

37. A method for treating animals in need of treatment comprising orally administering to said animals the solid dosage form of claim 26, wherein the effective amount of medicament is an amount to render said treatment.

38. A method for treating animals in need of treatment comprising orally administering to said animals the solid dosage form of claim 27, wherein the effective amount of medicament is an amount to render said treatment.

39. A method for treating animals in need of treatment comprising orally administering to said animals the solid dosage form of claim 28, wherein the effective amount of medicament is an amount to render said treatment.

40. A method for treating animals in need of treatment comprising orally administering to said animals the solid dosage form of claim 29, wherein the effective amount of medicament is an amount to render said treatment.

41. A method for treating animals in need of treatment comprising orally administering to said animals the solid dosage form of claim 30, wherein the effective amount of medicament is an amount to render said treatment.

42. A method for treating animals in need of treatment comprising orally administering to said animals the solid dosage form of claim 31, wherein the effective amount of medicament is an amount to render said treatment.

43. A method for treating animals in need of treatment comprising orally administering to said animals the solid dosage form of claim 32, wherein the effective amount of medicament is an amount to render said treatment.

44. A method for treating animals in need of treatment comprising orally administering to said animals the solid dosage form of claim 33, wherein the effective amount of medicament is an amount to render said treatment.

45. A method for treating animals in need of treatment comprising orally administering to said animals the solid dosage form of claim 34, wherein the effective amount of medicament is an amount to render said treatment.

* * * * *